US009687325B2

(12) United States Patent
Park et al.

(10) Patent No.: US 9,687,325 B2
(45) Date of Patent: Jun. 27, 2017

(54) METHOD OF MANUFACTURING ZIRCONIA BLOCK FOR ARTIFICIAL TOOTH HAVING COLOR GRADIENT

(71) Applicant: DMAX CO., LTD., Dalseo-gu, Daegu (KR)

(72) Inventors: Tae-Seok Park, Seoul (KR); In-Kon Chun, Gyeonggi-do (KR)

(73) Assignee: DMAX CO., LTD., Daegu (KR)

( * ) Notice: Subject to any disclaimer, the term of this patent is extended or adjusted under 35 U.S.C. 154(b) by 0 days.

(21) Appl. No.: 14/375,826

(22) PCT Filed: Jul. 19, 2013

(86) PCT No.: PCT/KR2013/006513
§ 371 (c)(1),
(2) Date: Jul. 31, 2014

(87) PCT Pub. No.: WO2014/137037
PCT Pub. Date: Sep. 12, 2014

(65) Prior Publication Data
US 2016/0000538 A1    Jan. 7, 2016

(30) Foreign Application Priority Data

Mar. 5, 2013  (KR) ........................ 10-2013-0023196

(51) Int. Cl.
*A61C 5/00* (2017.01)
*A61C 13/08* (2006.01)
(Continued)

(52) U.S. Cl.
CPC ........ *A61C 13/081* (2013.01); *A61C 13/0022* (2013.01); *A61C 13/083* (2013.01); *A61L 27/10* (2013.01); *A61C 13/09* (2013.01)

(58) Field of Classification Search
CPC .................................................. A61C 13/081
See application file for complete search history.

(56) References Cited

U.S. PATENT DOCUMENTS

| 4,207,678 A * | 6/1980 | Jeannette ............... A61C 19/10 433/203.1 |
| 2006/0008774 A1* | 1/2006 | Orth .................... A61C 13/0022 433/202.1 |

(Continued)

FOREIGN PATENT DOCUMENTS

| JP | 08119837 A | 5/1996 |
| JP | 2004035332 A | 2/2004 |

(Continued)

OTHER PUBLICATIONS

Office Action for related Japanese Application No. JP2015-531843; Office Action received Jan. 19, 2016.

*Primary Examiner* — Galen Hauth
(74) *Attorney, Agent, or Firm* — STIP Law Group, LLC (57) ABSTRACT

There is provided a method of manufacturing a zirconia block for an artificial tooth having a color gradient. The method includes: preparing colored zirconia-based powder and white zirconia-based powder; preparing a plurality of raw materials in which the colored zirconia-based powder and the white zirconia-based powder are mixed in different weight ratios by mixing the colored zirconia-based powder and the white zirconia-based powder while changing a mixing ratio in order to express a desired color gradient; sequentially injecting the plurality of raw materials into a compression mold or a mold frame to mold in increasing or decreasing order of content of the colored zirconia-based powder of the raw material; and calcining a molding result. According to the present invention, it is possible to express aesthetics of a natural tooth by implementing a color gradient of the natural tooth in the zirconia block itself without using porcelain powder or a liquid color set.

18 Claims, 2 Drawing Sheets

(51) Int. Cl.
    *A61L 27/10*     (2006.01)
    *A61C 13/083*     (2006.01)
    *A61C 13/00*     (2006.01)
    *A61C 13/09*     (2006.01)

(56) References Cited

U.S. PATENT DOCUMENTS

| | | |
|---|---|---|
| 2008/0085828 A1 | 4/2008 | Khan et al. |
| 2008/0303181 A1* | 12/2008 | Holand .................. A61O 5/10 264/16 |
| 2011/0189636 A1* | 8/2011 | Thiel .................. A61C 13/0022 433/199.1 |
| 2012/0196244 A1 | 8/2012 | Khan et al. |

FOREIGN PATENT DOCUMENTS

| | | |
|---|---|---|
| JP | 2011073907 A | 4/2011 |
| KR | 100650409 B1 | 11/2006 |
| KR | 100876059 B1 | 12/2008 |
| KR | 1020110121379 A | 11/2011 |

* cited by examiner

METHOD OF MANUFACTURING ZIRCONIA BLOCK FOR ARTIFICIAL TOOTH HAVING COLOR GRADIENT

TECHNICAL FIELD

The present invention relates to a method of manufacturing a zirconia block for an artificial tooth, and more specifically, to a method of manufacturing a zirconia block for an artificial tooth having a color gradient used in dental clinics or dental laboratories.

BACKGROUND ART

In order to replace a missing tooth or a tooth having a degraded function, dental clinics or dental laboratories manufacture an artificial tooth and use a zirconia material in general.

A zirconia artificial tooth has advantageous in that it has excellent biocompatibility, a greater aesthetic function than a metal, and high mechanical properties (flexure strength of 1,000 MPa or more and fracture toughness of 9 to 10 $MPa \cdot m^{1/2}$), it has high productivity since it can be automatically produced using a dental CAD/CAM system, and it can be used both in an anterior region and a posterior region.

When an artificial tooth is manufactured using zirconia, it is very important to preserve aesthetics by producing it to have a color as similar as possible to a natural tooth. In general, a tooth has various colors, and a color guide is used as a reference in many cases.

In a commonly used color guide, colors are classified as A series, B series, C series, D series, or the like. Even when a natural tooth belongs to A series, a concentration of the color is subdivided into a root of a tooth of A3, a body of A2, a cusp of A1, and the like. In order to express them, porcelain powder, a liquid color set, or the like is used.

Since a zirconia block color in the related art has a very simple form expressing white or only one particular color, in order to express the same color as a real natural tooth, several complex processes such as a pigment treatment and a surface treatment are necessary after the zirconia block is processed.

DISCLOSURE

Technical Problem

The present invention provides a method of manufacturing a zirconia block capable of expressing aesthetics of a natural tooth by implementing a color gradient of the natural tooth in the zirconia block itself without using porcelain powder or a liquid color set.

Technical Solution

The present invention provides a method of manufacturing a zirconia block for an artificial tooth having a color gradient. The method includes (a) preparing colored zirconia-based powder and white zirconia-based powder, (b) preparing a plurality of raw materials in which the colored zirconia-based powder and the white zirconia-based powder are mixed in different weight ratios by mixing the colored zirconia-based powder and the white zirconia-based powder while changing a mixing ratio in order to express a desired color gradient, (c) sequentially injecting the plurality of raw materials into a compression mold in increasing or decreasing order of content of the colored zirconia-based powder of the raw material, (d) applying a pressure to the compression mold into which the plurality of raw materials are injected to mold, and (e) calcining a molding result.

The method may further include performing a cold isostatic pressing (CIP) process in order to maintain a uniform internal density distribution of the molding result before the calcining, and a cold isostatic pressure in a range of 10 to 200 MPa may be preferably applied to the molding result.

The colored zirconia-based powder may be mixed with an organic binder and the organic binder being 0.1 to 7 parts by weight may be mixed relative to 100 parts by weight of the colored zirconia-based powder, and the white zirconia-based powder may be mixed with the organic binder, and the organic binder being 0.1 to 7 parts by weight may be mixed relative to 100 parts by weight of the white zirconia-based powder.

When the colored zirconia-based powder and the white zirconia-based powder are mixed in order to prepare the plurality of raw materials, the organic binder may be mixed together, and the organic binder being 0.1 to 7 parts by weight may be mixed relative to 100 parts by weight of each raw material.

The method may further include performing a de-binding process in order to remove an organic binder from the molding result before the calcining, and the de-binding process may be preferably performed at a temperature of 400 to 800° C.

In order to express the color gradient, the plurality of raw materials may include 7 to 20 raw materials in which the colored zirconia-based powder and the white zirconia-based powder are mixed in different ratios, and the molding result may preferably have a structure in which the 7 to 20 raw materials are sequentially stacked.

When the plurality of raw materials are observed as a whole, content of the colored zirconia-based powder may increase in a constant rate and content of the white zirconia-based powder corresponding to the content of the colored zirconia-based powder may decrease in a constant rate, or content of the colored zirconia-based powder may decrease in a constant rate and content of the white zirconia-based powder corresponding to the content of the colored zirconia-based powder may increase in a constant rate, and in the operation (c), the plurality of raw materials may be sequentially injected in order of increasing content of the colored zirconia-based powder in a constant rate and decreasing content of the white zirconia-based powder corresponding to the content of the colored zirconia-based powder in a constant rate, or may be sequentially injected in order of decreasing content of the colored zirconia-based powder in a constant rate and increasing content of the white zirconia-based powder corresponding to the content of the colored zirconia-based powder in a constant rate.

The colored zirconia-based powder may be powder formed such that zirconia powder and a metal oxide for expressing colors are mixed and go through a sintering process, and the metal oxide may be made of at least one material selected from among red iron oxide ($Fe_2O_3$), yellow iron oxide ($Fe_2O_3$), $MoO_3$, $MnO_2$, $CeO_2$, $BaO$, $V_2O_5$, $V_2O_3$, and $CoO$.

The calcining may be preferably performed at a temperature of 800 to 1100° C. under an oxidizing atmosphere.

The present invention also provides a method of manufacturing a zirconia block for an artificial tooth having a color gradient. The method includes (a) preparing colored zirconia-based powder and white zirconia-based powder, (b) preparing a plurality of raw materials in which the colored zirconia-based powder and the white zirconia-based powder are mixed in different weight ratios by mixing the colored zirconia-based powder and the white zirconia-based powder while changing a mixing ratio in order to express a desired color gradient, (c) sequentially injecting the plurality of raw materials into a mold frame along with a liner to mold in increasing or decreasing order of content of the colored zirconia-based powder of the raw material, (d) de-molding a molding result from the mold frame, and (e) calcining the de-molded mold result.

The method may further include performing a cold isostatic pressing (CIP) process in order to maintain a uniform internal density distribution of the molding result before the calcining, and a cold isostatic pressure in a range of 10 to 200 MPa may be preferably applied to the molding result.

The colored zirconia-based powder may be mixed with an organic binder and the organic binder being 0.1 to 7 parts by weight may be mixed relative to 100 parts by weight of the colored zirconia-based powder, and the white zirconia-based powder may be mixed with the organic binder and the organic binder being 0.1 to 7 parts by weight may be mixed relative to 100 parts by weight of the white zirconia-based powder.

When the colored zirconia-based powder and the white zirconia-based powder are mixed in order to prepare the plurality of raw materials, the organic binder may be mixed together, and the organic binder being 0.1 to 7 parts by weight may be mixed relative to 100 parts by weight of each raw material.

The method may further include performing a de-binding process in order to remove the organic binder from the molding result before the calcining, and the de-binding process may be preferably performed at a temperature of 400 to 800° C.

In order to express the color gradient, the plurality of raw materials may include 7 to 20 raw materials in which the colored zirconia-based powder and the white zirconia-based powder are mixed in different ratios, and the molding result may preferably have a structure in which the 7 to 20 raw materials are sequentially stacked.

When the plurality of raw materials are observed as a whole, content of the colored zirconia-based powder may increase in a constant rate and content of the white zirconia-based powder corresponding to the content of the colored zirconia-based powder may decrease in a constant rate, or content of the colored zirconia-based powder may decrease in a constant rate and content of the white zirconia-based powder corresponding to the content of the colored zirconia-based powder may increase in a constant rate, and in the operation (c), the plurality of raw materials may be sequentially injected in order of increasing content of the colored zirconia-based powder in a constant rate and decreasing content of the white zirconia-based powder corresponding to the content of the colored zirconia-based powder in a constant rate, or may be sequentially injected in order of decreasing content of the colored zirconia-based powder in a constant rate and increasing content of the white zirconia-based powder corresponding to the content of the colored zirconia-based powder in a constant rate.

The colored zirconia-based powder may be powder formed such that zirconia powder and a metal oxide for expressing colors are mixed and go through a sintering process, and the metal oxide may be made of at least one material selected from among red iron oxide ($Fe_2O_3$), yellow iron oxide ($Fe_2O_3$), $MoO_3$, $MnO_2$, $CeO_2$, $BaO$, $V_2O_5$, $V_2O_3$, and $CoO$.

The calcining may be preferably performed at a temperature of 800 to 1100° C. under an oxidizing atmosphere.

Advantageous Effects

According to the present invention, it is possible to express aesthetics of a natural tooth by implementing a color gradient of the natural tooth in a zirconia block itself without using porcelain powder or a liquid color set.

Since the same color gradient as the natural tooth can be obtained, operations for expressing the same color as the natural tooth such as a pigment treatment and a surface treatment are unnecessary after the zirconia block is processed. Therefore, it is possible to significantly reduce an operation time and manufacture a high quality artificial tooth. From the point of view of clinical practitioners, it is possible to conveniently perform a procedure according to oral conditions of patients without concern of a color change, and the original color can be maintained after the procedure since the block itself has a color gradient. Accordingly, it is possible to maximize patients' satisfaction.

When the zirconia block having the same color gradient as the natural tooth is used, an operator can save about 30% of a process time and can dedicate to manufacture a high quality prosthesis. From the point of view of practitioners, it is possible to conveniently perform a procedure according to oral conditions of patients since there is no concern of a color change.

In addition, the original color can be maintained after the procedure since the block itself has a color gradient. Accordingly, it is possible to increase patients' satisfaction.

MODES OF THE INVENTION

According to an aspect of the present invention, there is provided a method of manufacturing a zirconia block for an artificial tooth having a color gradient. The method includes (a) preparing colored zirconia-based powder and white zirconia-based powder, (b) preparing a plurality of raw materials in which the colored zirconia-based powder and the white zirconia-based powder are mixed in different weight ratios by mixing the colored zirconia-based powder and the white zirconia-based powder while changing a mixing ratio in order to express a desired color gradient, (c) sequentially injecting the plurality of raw materials into a compression mold in increasing or decreasing order of content of the colored zirconia-based powder, (d) applying a pressure to the compression mold into which the plurality of raw materials are injected to mold, and (e) calcining a molding result.

According to another aspect of the present invention, there is provided a method of manufacturing a zirconia block for an artificial tooth having a color gradient. The method includes (a) preparing colored zirconia-based powder and white zirconia-based powder, (b) preparing a plurality of raw materials in which the colored zirconia-based powder and the white zirconia-based powder are mixed in different weight ratios by mixing the colored zirconia-based powder and the white zirconia-based powder while changing a mixing ratio in order to express a desired color gradient, (c) sequentially injecting the plurality of raw materials into a mold frame powder along with a liner to mold in increasing or decreasing order of content of the colored zirconia-based powder of the raw material, (d) de-molding a molding result from the mold frame, and (e) calcining the de-molded mold result.

Hereinafter, preferred examples of the present invention will be described in detail with reference to the accompanying drawings. However, the following examples are provided for those skilled in the art to sufficiently understand the present invention, may be modified in various other forms, and the scope of the present invention is not limited to the following examples. The same numerals in the drawings denote the same elements.

Hereinafter, the term "color" refers to colors other than white, and includes a chromatic color and an achromatic color other than white.

Zirconium (Zr) is a transition metal belonging to a titanium family and period 5 in the periodic table, and is an element having extremely high corrosion resistance to acid and alkali. An oxide of such zirconium is a zirconium dioxide, which is commonly called zirconia. Zirconia ($ZrO_2$) has excellent properties such as high strength, thermal stability, and high corrosion resistance.

A zirconia block is used as a material of an artificial tooth, is more similar to a natural tooth than an existing prosthesis made of porcelain powder and gold, and an excellent aesthetic effect. In addition, the zirconia block has excellent biocompatibility, has no inflammation or allergy, and is a semipermanent material that has no deformation and discoloration in any food intake without erosion. Since the zirconia block has low thermal conductivity, it has low sensitivity to cold and heat. Therefore, patients are highly satisfied with the material.

According to a commonly used color guide, colors are classified as A series, B series, C series, D series, or the like. Even when a natural tooth belongs to A series, a concentration of the color is subdivided into a root of a tooth of A3, a body of A2, a cusp of A1, and the like. In order to express them, porcelain powder, a liquid color set, or the like is used.

Since a zirconia block color in the related art has a very simple form expressing white or only one particular color, in order to express the same color as a real natural tooth, several complex processes such as a pigment treatment and a surface treatment are necessary after the zirconia block is processed.

When the zirconia block has the same color gradient as the natural tooth, operations for expressing the same color as the natural tooth such as a pigment treatment and a surface treatment are unnecessary after the zirconia block is processed. Therefore, it is possible to significantly reduce an operation time and manufacture a high quality artificial tooth. From the point of view of clinical practitioners, it is possible to conveniently perform a procedure according to oral conditions of patients without concern of a color change, and the original color can be maintained after the procedure since the block itself has a color gradient. Accordingly, it is possible to maximize patients' satisfaction.

In order to manufacture the zirconia block having a natural color gradient, a colored zirconia-based raw material (colored raw material) and a white zirconia-based raw material (white raw material) are mixed in an appropriate component ratio, are molded in a mold or a manufacturing container having a shape to be molded according to an appropriate component ratio through a compression molding or slip casting method, and a molding body is de-bound, and calcined.

According to a first preferred example of the present invention, there is provided a method of manufacturing a zirconia block for an artificial tooth having a color gradient. The method includes (a) preparing colored zirconia-based powder and white zirconia-based powder, (b) preparing a plurality of raw materials in which the colored zirconia-based powder and the white zirconia-based powder are mixed in different weight ratios by mixing the colored zirconia-based powder and the white zirconia-based powder while changing a mixing ratio in order to express a desired color gradient, (c) sequentially injecting the plurality of raw materials into a compression mold in increasing or decreasing order of content of the colored zirconia-based powder of the raw material, (d) applying a pressure to the compression mold into which the plurality of raw materials are injected to mold, and (e) calcining a molding result.

According to a second preferred example of the present invention, there is provided a method of manufacturing a zirconia block for an artificial tooth having a color gradient. The method includes (a) preparing colored zirconia-based powder and white zirconia-based powder, (b) preparing a plurality of raw materials in which the colored zirconia-based powder and the white zirconia-based powder are mixed in different weight ratios by mixing the colored zirconia-based powder and the white zirconia-based powder while changing a mixing ratio in order to express a desired color gradient, (c) sequentially injecting the plurality of raw materials into a mold frame along with a liner to mold in increasing or decreasing order of content of the colored zirconia-based powder of the raw material, (d) de-molding a molding result from the mold frame, and (e) calcining the de-molded mold result.

The method may further include performing a cold isostatic pressing (CIP) process in order to maintain a uniform internal density distribution of the molding result before the calcining A cold isostatic pressure in a range of 10 to 200 MPa is preferably applied to the molding result.

The colored zirconia-based powder is mixed with an organic binder. The organic binder being 0.1 to 7 parts by weight is mixed relative to 100 parts by weight of the colored zirconia-based powder. The white zirconia-based powder is mixed with the organic binder. The organic binder being 0.1 to 7 parts by weight is mixed relative to 100 parts by weight of the white zirconia-based powder.

When the colored zirconia-based powder and the white zirconia-based powder are mixed in order to prepare the plurality of raw materials, the organic binder is mixed together. The organic binder being 0.1 to 7 parts by weight may be mixed relative to 100 parts by weight of each raw material.

The method may further include performing a de-binding process in order to remove the organic binder from the molding result before the calcining. The de-binding process is preferably performed at a temperature of 400 to 800° C.

In order to express the color gradient, the plurality of raw materials include 7 to 20 raw materials in which the colored zirconia-based powder and the white zirconia-based powder are mixed in different ratios. The molding result preferably has a structure in which the 7 to 20 raw materials are sequentially stacked.

When the plurality of raw materials are observed as a whole, content of the colored zirconia-based powder may increase in a constant rate and content of the white zirconia-based powder corresponding to the content of the colored zirconia-based powder may decrease in a constant rate, or content of the colored zirconia-based powder may decrease in a constant rate and content of the white zirconia-based powder corresponding to the content of the colored zirconia-based powder may increase in a constant rate. In the operation (c), the plurality of raw materials may be sequentially injected in order of increasing content of the colored zirconia-based powder in a constant rate and decreasing content of the white zirconia-based powder corresponding to the content of the colored zirconia-based powder in a constant rate, or may be sequentially injected in order of decreasing content of the colored zirconia-based powder in a constant rate and increasing content of the white zirconia-based powder corresponding to the content of the colored zirconia-based powder in a constant rate.

The colored zirconia-based powder is powder formed such that zirconia powder and a metal oxide for expressing colors are mixed and go through a sintering process. The metal oxide may be made of at least one material selected from among red iron oxide ($Fe_2O_3$), yellow iron oxide ($Fe_2O_3$), $MoO_3$, $MnO_2$, $CeO_2$, $BaO$, $V_2O_5$, $V_2O_3$, and $CoO$.

The calcining is preferably performed at a temperature of 800 to 1100° C. under an oxidizing atmosphere.

When a zirconia block having various color gradients is manufactured, various raw materials may also be used in addition to the colored zirconia-based powder and the white zirconia-based powder.

Hereinafter, examples according to the present invention will be provided, but the present invention is not limited to the following examples.

EXAMPLE 1

A method of manufacturing a zirconia block having a color gradient using a compression molding method will be described.

Colored zirconia-based powder and white zirconia-based powder are prepared. The zirconia-based powder is selected in consideration of a shape, molding conditions, a powder size, a mixing component, and the like. For example, the zirconia-based powder preferably has an average particle size of about 100 nm to 10 μm, and preferably has a spherical shape.

The white zirconia-based powder is white zirconia powder having no color. In order to easily mold, an organic binder may be added and mixed with the white zirconia-based powder. In this case, the organic binder being 0.1 to 7 parts by weight is preferably added relative to 100 parts by weight of the white zirconia-based powder. As the organic binder, a generally known material such as polyvinyl alcohol (PVA) may be used, but the invention is not limited thereto.

The colored zirconia-based powder may be powder formed such that zirconia powder and a metal oxide for expressing colors are mixed and go through a sintering process. As the metal oxide for expressing colors, red iron oxide ($Fe_2O_3$), yellow iron oxide ($Fe_2O_3$), $MoO_3$ for expressing yellow, $MnO_2$ for expressing ivory or brown, $CeO_2$ for expressing yellow, $BaO$ for expressing yellow, $V_2O_5$ for expressing an orange color, $V_2O_3$ for expressing black, $CoO$ for expressing black, or mixtures thereof may be used. In order to easily mold, the organic binder may be added and mixed with the colored zirconia-based powder. In this case, the organic binder being 0.1 to 7 parts by weight is preferably added relative to 100 parts by weight of the colored zirconia-based powder. As the organic binder, a generally known material such as polyvinyl alcohol (PVA) may be used, but the invention is not limited thereto.

A plurality of raw materials in which the colored zirconia-based powder and the white zirconia-based powder are mixed in different weight ratios by mixing the colored zirconia-based powder and the white zirconia-based powder while changing a mixing ratio in order to express a desired color gradient are prepared. In the plurality of raw materials, an amount of the colored zirconia-based powder and an amount of the white zirconia-based powder have a sequential ratio in order to express a desired color gradient. In this case, a mixing ratio of the colored zirconia-based powder and the white zirconia-based powder may be regulated in several to several tens of steps according to the desired color gradient. When the plurality of raw materials are observed as a whole, content of the colored zirconia-based powder may increase in a constant rate and content of the white zirconia-based powder corresponding to the content of the colored zirconia-based powder may decrease in a constant rate, or content of the colored zirconia-based powder may decrease in a constant rate and content of the white zirconia-based powder corresponding to the content of the colored zirconia-based powder may increase in a constant rate. For example, as shown in the following Table 1, raw materials 1 to 10 in which the colored zirconia-based powder and the white zirconia-based powder are mixed in different weight ratios are prepared.

TABLE 1

| Raw material name | Weight ratio of colored zirconia-based powder | Weight ratio of white zirconia-based powder |
|---|---|---|
| raw material 1 | 10 | 0 |
| raw material 2 | 9 | 1 |
| raw material 3 | 8 | 2 |
| raw material 4 | 7 | 3 |
| raw material 5 | 6 | 4 |
| raw material 6 | 5 | 5 |
| raw material 7 | 4 | 6 |
| raw material 8 | 3 | 7 |
| raw material 9 | 2 | 8 |
| raw material 10 | 1 | 9 |

For example, a raw material 1 is prepared by mixing the colored zirconia-based powder and the white zirconia powder in a weight ratio of 10:0. A raw material 2 is prepared by mixing the colored zirconia-based powder and the white zirconia powder in a weight ratio of 9:1. A raw material 3 is prepared by mixing the colored zirconia-based powder and the white zirconia powder in a weight ratio of 8:2. A raw material 4 is prepared by mixing the colored zirconia-based powder and the white zirconia powder in a weight ratio of 7:3. A raw material 5 is prepared by mixing the colored zirconia-based powder and the white zirconia powder in a weight ratio of 6:4. A raw material 6 is prepared by mixing the colored zirconia-based powder and the white zirconia powder in a weight ratio of 5:5. A raw material 7 is prepared by mixing the colored zirconia-based powder and the white zirconia powder in a weight ratio of 4:6. A raw material 8 is prepared by mixing the colored zirconia-based powder and the white zirconia powder in a weight ratio of 3:7. A raw material 9 is prepared by mixing the colored zirconia-based powder and the white zirconia powder in a weight ratio of 2:8. A raw material 10 is prepared by mixing the colored zirconia-based powder and the white zirconia powder in a weight ratio of 1:9. When the organic binder is not added and mixed with the colored zirconia-based powder and the white zirconia-based powder, the organic binder is added and mixed in this operation. In this case, the organic binder of 0.1 to 7 parts by weight is preferably added relative to 100 parts by weight of total content of the colored zirconia-based powder and the white zirconia-based powder. As the organic binder, a generally known material such as polyvinyl alcohol (PVA) may be used, but the invention is not limited thereto.

Figure 1:
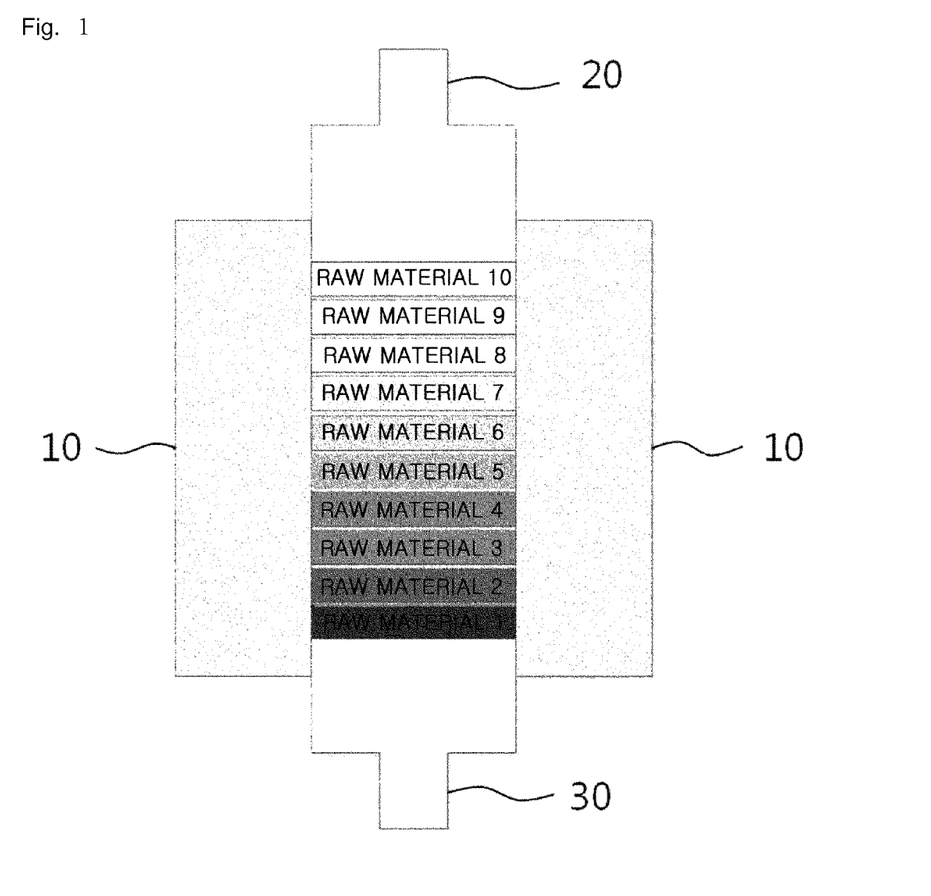
FIG. 1 is a diagram illustrating a state in which 10 raw materials are sequentially stacked in a compression mold in increasing order of content of colored zirconia-based powder of the raw material.

A compression mold 10 is prepared to mold the zirconia-based powder. The compression mold 10 may include an upper punch 20 and a lower punch 30. In order to express a desired color gradient, the plurality of raw materials in which the colored zirconia-based powder and the white zirconia-based powder are mixed in a target ratio are injected into the mold 10.

As illustrated in FIG. 1, the plurality of raw materials are sequentially injected into the compression mold 10 by classifying the mixing ratio of the colored zirconia-based powder and the white zirconia-based powder as a plurality of steps. In this case, the plurality of steps may be regulated as several to several tens of steps according to a desired color gradient. The plurality of raw materials are sequentially injected into the compression mold 10 in increasing or decreasing order of content of the colored zirconia-based powder of the raw material. The plurality of raw materials are sequentially injected in order of increasing content of the colored zirconia-based powder in a constant rate and decreasing content of the white zirconia-based powder corresponding to the content of the colored zirconia-based powder in a constant rate, or are preferably sequentially injected in order of decreasing content of the colored zirconia-based powder in a constant rate and increasing content of the white zirconia-based powder corresponding to the content of the colored zirconia-based powder in a constant rate.

Table 1 includes mixing ratios having 10 steps, and mixing ratios of the raw materials 1 to 10 are exemplified in Table 1. For example, the raw material 1 disposed at the bottom of the compression mold 10 uses a material in which the colored zirconia-based powder and the white zirconia powder are mixed in a weight ratio of 10:0. The raw material 2 disposed above the raw material 1 uses a material in which the colored zirconia-based powder and the white zirconia powder are mixed in a weight ratio of 9:1. The raw material 3 disposed above the raw material 2 uses a material in which the colored zirconia-based powder and the white zirconia powder are mixed in a weight ratio of 8:2. The raw material 4 disposed above the raw material 3 uses a material in which the colored zirconia-based powder and the white zirconia powder are mixed in a weight ratio of 7:3. The raw material 5 disposed above the raw material 4 uses a material in which the colored zirconia-based powder and the white zirconia powder are mixed in a weight ratio of 6:4. The raw material 6 disposed above the raw material 5 uses a material in which the colored zirconia-based powder and the white zirconia powder are mixed in a weight ratio of 5:5. The raw material 7 disposed above the raw material 6 uses a material in which the colored zirconia-based powder and the white zirconia powder are mixed in a weight ratio of 4:6. The raw material 8 disposed above the raw material 7 uses a material in which the colored zirconia-based powder and the white zirconia powder are mixed in a weight ratio of 3:7. The raw material 9 disposed above the raw material 8 uses a material in which the colored zirconia-based powder and the white zirconia powder are mixed in a weight ratio of 2:8. The raw material 10 disposed above the raw material 9 uses a material in which the colored zirconia-based powder and the white zirconia powder are mixed in a weight ratio of 1:9.

The mold 10 into which the plurality of raw materials are injected is compressed and molded in a target shape by applying a predetermined pressure (for example, a pressure of 1 to 3 tons) using a press.

In order to maintain a uniform internal density distribution of the molding result, a cold isostatic pressing (CIP) process is performed. A cold isostatic pressure in a range of 10 to 200 MPa is preferably applied to the compression molding result for 1 to 120 minutes.

A de-binding process is performed to burn and remove the binder and the like from the compression molding result. The de-binding process is preferably performed at a temperature of about 400 to 800° C. for 1 to 120 hours. In addition, the de-binding process is preferably performed under an oxidizing (oxygen ($O_2$) or air) atmosphere.

In order to match hardness and density conditions appropriate for mechanical processing after the de-binding process, the result is charged in a furnace such as an electric furnace and a calcining process is performed. The calcining process is preferably performed at a calcination temperature of about 800 to 1100° C. for about 10 minutes to 48 hours. The temperature is preferably increased up to the calcining temperature in a heating rate of 1 to 50° C./min. When the heating rate is too low, it takes a great amount of time, thereby decreasing productivity. When the heating rate is too high, thermal stress may occur due to a rapid temperature increase. Accordingly, the temperature is preferably increased in the range of the heating rate. The calcining is preferably performed under an oxidizing atmosphere (for example, an oxygen ($O_2$) or air atmosphere). After the calcining process is performed, the temperature of the furnace is decreased to unload the calcined result. The furnace may be cooled naturally by blocking power of the furnace, or cooled by arbitrarily setting a temperature decrease rate (for example, 10° C./min). It is preferable that the pressure in the furnace be constantly maintained even while the temperature of the furnace is decreased. The binder remaining in the calcining process is removed by burning.

The calcined result is loaded on a miller such as a computerized numerical controller (CNC) and is processed according to a target shape of the zirconia block. A computer-aided design (CAD)/computer-aided manufacturing (CAM) process may be used for the processing.

The processed result is cleaned and dried. The drying is preferably performed at a temperature of about a room temperature to 150° C. for 10 minutes to 24 hours.

EXAMPLE 2

A method of manufacturing a zirconia block having a color gradient using a slip casting method will be described.

Colored zirconia-based powder and white zirconia-based powder are prepared. The zirconia-based powder is selected in consideration of a shape, molding conditions, a powder size, a mixing component, and the like. For example, the zirconia-based powder preferably has an average particle size of about 100 nm to 10 μm, and preferably has a spherical shape.

The white zirconia-based powder is white zirconia-based powder having no color. In order to easily mold, an organic binder may be added and mixed with the white zirconia-based powder. In this case, the organic binder being 0.1 to 7 parts by weight is preferably added relative to 100 parts by weight of the white zirconia-based powder. As the organic binder, a generally known material such as polyvinyl alcohol (PVA) may be used, but the invention is not limited thereto.

The colored zirconia-based powder may be powder formed such that zirconia powder and a metal oxide for expressing colors are mixed and go through a sintering process. As the metal oxide for expressing colors, red iron oxide ($Fe_2O_3$), yellow iron oxide ($Fe_2O_3$), $MoO_3$ for expressing yellow, $MnO_2$ for expressing ivory or brown, $CeO_2$ for expressing yellow, BaO for expressing yellow, $V_2O_5$ for expressing an orange color, $V_2O_3$ for expressing black, CoO for expressing black, or mixtures thereof may be used. In order to easily mold, the organic binder may be added and mixed with the colored zirconia-based powder. In this case, the organic binder being 0.1 to 7 parts by weight is preferably added relative to 100 parts by weight of the colored zirconia-based powder. As the organic binder, a generally known material such as polyvinyl alcohol (PVA) may be used, but the invention is not limited thereto.

A plurality of raw materials in which the colored zirconia-based powder and the white zirconia-based powder are mixed in different weight ratios by mixing the colored zirconia-based powder and the white zirconia-based powder while changing a mixing ratio in order to express a desired color gradient are prepared. In the plurality of raw materials, an amount of the colored zirconia-based powder and an amount of the white zirconia-based powder have a sequential ratio in order to express a desired color gradient. In this case, a mixing ratio of the colored zirconia-based powder and the white zirconia-based powder may be regulated in several to several tens of steps according to the desired color gradient. When the plurality of raw materials are observed as a whole, content of the colored zirconia-based powder may increase in a constant rate and content of the white zirconia-based powder corresponding to the content of the colored zirconia-based powder may decrease in a constant rate, or content of the colored zirconia-based powder may decrease in a constant rate and content of the white zirconia-based powder corresponding to the content of the colored zirconia-based powder may increase in a constant rate.

For example, as shown in Table 1, raw materials 1 to 10 in which the colored zirconia-based powder and the white zirconia-based powder are mixed in different weight ratios are prepared. For example, a raw material 1 is prepared by mixing the colored zirconia-based powder and the white zirconia powder in a weight ratio of 10:0. A raw material 2 is prepared by mixing the colored zirconia-based powder and the white zirconia powder in a weight ratio of 9:1. A raw material 3 is prepared by mixing the colored zirconia-based powder and the white zirconia powder in a weight ratio of 8:2. A raw material 4 is prepared by mixing the colored zirconia-based powder and the white zirconia powder in a weight ratio of 7:3. A raw material 5 is prepared by mixing the colored zirconia-based powder and the white zirconia powder in a weight ratio of 6:4. A raw material 6 is prepared by mixing the colored zirconia-based powder and the white zirconia powder in a weight ratio of 5:5. A raw material 7 is prepared by mixing the colored zirconia-based powder and the white zirconia powder in a weight ratio of 4:6. A raw material 8 is prepared by mixing the colored zirconia-based powder and the white zirconia powder in a weight ratio of 3:7. A raw material 9 is prepared by mixing the colored zirconia-based powder and the white zirconia powder in a weight ratio of 2:8. A raw material 10 is prepared by mixing the colored zirconia-based powder and the white zirconia powder in a weight ratio of 1:9. When the organic binder is not added and mixed with the colored zirconia-based powder and the white zirconia-based powder, the organic binder is added and mixed in this operation. In this case, the organic binder being 0.1 to 7 parts by weight is preferably added relative to 100 parts by weight of total content of the colored zirconia-based powder and the white zirconia-based powder. As the organic binder, a generally known material such as polyvinyl alcohol (PVA) may be used, but the invention is not limited thereto.

Figure 2:
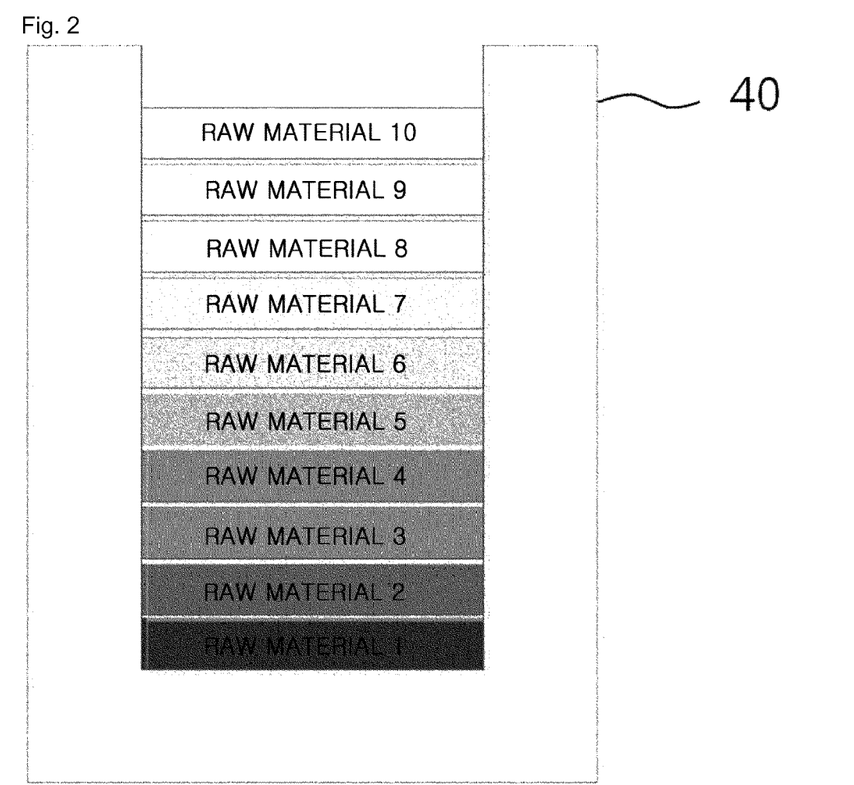
FIG. 2 is a diagram illustrating a state in which 10 raw materials are sequentially stacked in a mold frame in increasing order of content of colored zirconia-based powder of the raw material.

A mold frame having a target shape is prepared. In order to express a desired color gradient, a plurality of raw materials in which the colored zirconia-based powder and the white zirconia-based powder are mixed in a target ratio and a liner are injected into a mold frame 40.

As illustrated in FIG. 2, the plurality of raw materials are sequentially injected into the mold frame 40 by classifying the mixing ratio of the colored zirconia-based powder and the white zirconia-based powder as a plurality of steps, along with the liner. In this case, the plurality of steps may be regulated as several to several tens of steps according to a desired color gradient. The plurality of raw materials are sequentially injected into the mold frame 40 in increasing or decreasing order of content of the colored zirconia-based powder of the raw material. The plurality of raw materials are sequentially injected in order of increasing content of the colored zirconia-based powder in a constant rate and decreasing content of the white zirconia-based powder corresponding to the content of the colored zirconia-based powder in a constant rate, or are preferably sequentially injected in order of decreasing content of the colored zirconia-based powder in a constant rate and increasing content of the white zirconia-based powder corresponding to the content of the colored zirconia-based powder in a constant rate.

Table 1 includes mixing steps having 10 steps and mixing ratios of the raw materials 1 to 10 are exemplified in Table 1.

For example, the raw material 1 disposed at the bottom of the mold frame 40 uses a material in which the colored zirconia-based powder and the white zirconia powder are mixed in a weight ratio of 10:0. The raw material 2 disposed above the raw material 1 uses a material in which the colored zirconia-based powder and the white zirconia powder are mixed in a weight ratio of 9:1. The raw material 3 disposed above the raw material 2 uses a material in which the colored zirconia-based powder and the white zirconia powder are mixed in a weight ratio of 8:2. The raw material 4 disposed above the raw material 3 uses a material in which the colored zirconia-based powder and the white zirconia powder are mixed in a weight ratio of 7:3. The raw material 5 disposed above the raw material 4 uses a material in which the colored zirconia-based powder and the white zirconia powder are mixed in a weight ratio of 6:4. The raw material 6 disposed above the raw material 5 uses a material in which the colored zirconia-based powder and the white zirconia powder are mixed in a weight ratio of 5:5. The raw material 7 disposed above the raw material 6 uses a material in which the colored zirconia-based powder and the white zirconia powder are mixed in a weight ratio of 4:6. The raw material 8 disposed above the raw material 7 uses a material in which the colored zirconia-based powder and the white zirconia powder are mixed in a weight ratio of 3:7. The raw material 9 disposed above the raw material 8 uses a material in which the colored zirconia-based powder and the white zirconia powder are mixed in a weight ratio of 2:8. The raw material 10 disposed above the raw material 9 uses a material in which the colored zirconia-based powder and the white zirconia powder are mixed in a weight ratio of 1:9.

As the liner, water may be used, but alcohol and the like may be used rather than water. In this case, a ratio of the raw material and the liner, which are injected into the mold frame

40, is preferably a ratio of 30 to 50 wt % raw material and 50 to 70 wt % liner. The raw material of the mold frame 40 may use plaster, but the material is not limited to the plaster.

When the plaster is used as the mold frame 40, if a mixture of the raw material and the liner is injected into the mold frame 40, the mold frame 40 attracts powder suspended in the water to a surface of the mold frame 40 along with the liner. At this time, the attracted liner is diffused and absorbed in the plaster, and a mixture layer having low water is formed on the surface of the mold frame 40. This mixture layer becomes hard over time. As a setting time becomes longer, the mixture layer becomes thicker, and a desired shape is obtained.

The molding result is de-molded from the mold frame 40.

A cold isostatic pressing (CIP) process is performed to maintain a uniform internal density distribution of the de-molded mold result. A cold isostatic pressure in a range of 10 to 200 MPa is preferably applied to a compressed molding result for 1 to 120 minutes.

A de-binding process is performed to burn and remove the binder and the like from the molding result. The de-binding process is preferably performed at a temperature of about 400 to 800° C. for 1 to 120 hours. In addition, the de-binding process is preferably performed under an oxidizing (oxygen ($O_2$) or air) atmosphere.

In order to match hardness and density conditions appropriate for mechanical processing after the de-binding process, the result is charged in a furnace such as an electric furnace and a calcining process is performed. The calcining process is preferably performed at a calcination temperature of about 800 to 1100° C. for about 10 minutes to 48 hours. The temperature is preferably increased up to the calcining temperature in a heating rate of 1 to 50° C./min. When the heating rate is too low, it takes a great amount of time, thereby decreasing productivity. When the heating rate is too high, thermal stress may occur due to a rapid temperature increase. Accordingly, the temperature is preferably increased in the range of the heating rate. The calcining is preferably performed under an oxidizing atmosphere (for example, an oxygen ($O_2$) or air atmosphere). After the calcining process is performed, the temperature of the furnace is decreased to unload the calcined result. The furnace may be cooled naturally by blocking power of the furnace, or cooled by arbitrarily setting a temperature decrease rate (for example, 10° C./min). It is preferable that the pressure in the furnace be constantly maintained even while the temperature of the furnace is decreased. The binder remaining in the calcining process is removed by burning.

The calcined result is loaded on a miller such as a computerized numerical controller (CNC) and is processed according to a target shape of the zirconia block. A computer-aided design (CAD)/computer-aided manufacturing (CAM) process may be used for the processing.

The processed result is cleaned and dried. The drying is preferably performed at a temperature of about a room temperature to 150° C. for 10 minutes to 24 hours.

Hereinafter, an example according to the present invention will be described, but the invention is not limited to the following example.

EXAMPLE

Colored zirconia-based powder and white zirconia-based powder were prepared.

As the white zirconia-based powder, white zirconia powder having a spherical shape and an average particle size of about 0.2 µm was used. In order to easily mold, an organic binder was added and mixed with the white zirconia-based powder. The organic binder being 3 parts by weight was mixed relative to 100 parts by weight of the white zirconia-based powder. PVA205MB (Japan, Kuraray) was used as the organic binder.

As the colored zirconia-based powder, powder formed such that zirconia and *** metal oxide for expressing colors are mixed and go through a sintering process was used. In order to easily mold, an organic binder was added and mixed with the colored zirconia-based powder. The organic binder being 3 parts by weight was mixed relative to 100 parts by weight of the white zirconia-based powder. PVA205MB (Japan, Kuraray) was used as the organic binder.

In order to express a desired color gradient, 10 raw materials in which the colored zirconia-based powder and the white zirconia-based powder are mixed in different weight ratios by mixing the colored zirconia-based powder and the white zirconia-based powder while changing a mixing ratio were prepared. As shown in Table 1, raw materials 1 to 10 in which the colored zirconia-based powder and the white zirconia-based powder are mixed in different weight ratios were prepared. In the plurality of raw materials, an amount of the colored zirconia-based powder and an amount of the white zirconia-based powder had a sequential ratio in order to express a desired color gradient.

A compression mold was prepared to mold the zirconia-based powder. In order to express a desired color gradient, an amount of the colored zirconia-based powder and an amount of the white zirconia-based powder were mixed in ratios illustrated in FIG. 1 and Table 1 and injected into the mold. The raw material 1 disposed at the bottom of the mold used a material in which the colored zirconia-based powder and the white zirconia powder are mixed in a weight ratio of 10:0. The raw material 2 disposed above the raw material 1 used a material in which the colored zirconia-based powder and the white zirconia powder are mixed in a weight ratio of 9:1. The raw material 3 disposed above the raw material 2 used a material in which the colored zirconia-based powder and the white zirconia powder are mixed in a weight ratio of 8:2. The raw material 4 disposed above the raw material 3 used a material in which the colored zirconia-based powder and the white zirconia powder are mixed in a weight ratio of 7:3. The raw material 5 disposed above the raw material 4 used a material in which the colored zirconia-based powder and the white zirconia powder are mixed in a weight ratio of 6:4. The raw material 6 disposed above the raw material 5 used a material in which the colored zirconia-based powder and the white zirconia powder are mixed in a weight ratio of 5:5. The raw material 7 disposed above the raw material 6 used a material in which the colored zirconia-based powder and the white zirconia powder are mixed in a weight ratio of 4:6. The raw material 8 disposed above the raw material 7 used a material in which the colored zirconia-based powder and the white zirconia powder are mixed in a weight ratio of 3:7. The raw material 9 disposed above the raw material 8 used a material in which the colored zirconia-based powder and the white zirconia powder are mixed in a weight ratio of 2:8. The raw material 10 disposed above the raw material 9 used a material in which the colored zirconia-based powder and the white zirconia powder are mixed in a weight ratio of 1:9.

The mold was compressed and molded by applying a pressure of 2 tons using a press.

In order to maintain a uniform internal density distribution of the molding result, a cold isostatic pressing (CIP)

process was performed. A cold isostatic pressure in a range of 100 MPa was applied to the compression molding result for 10 minutes.

A de-binding process was performed to remove the binder and the like from the molding result. The de-binding process was performed at a temperature of 600° C. for 60 hours.

In order to match hardness and density conditions appropriate for mechanical processing after the de-binding process, the result was charged in an electric furnace and a calcining process was performed. The calcining process was performed at a calcination temperature of about 1000° C. for 4 hours. The temperature was increased up to the calcining temperature in a heating rate of 5° C./min. The calcining was performed under an air atmosphere. The electric furnace was cooled naturally by blocking power.

Figure 3:
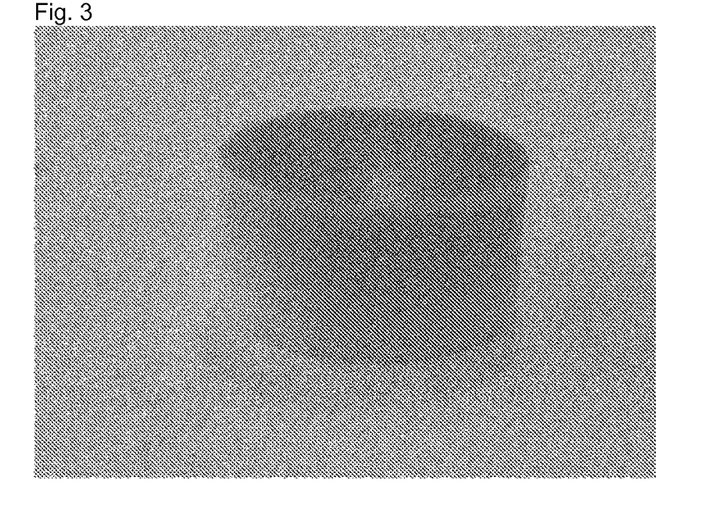
FIG. 3 is a picture showing a zirconia block having a color gradient manufactured according to an example.

The zirconia block having a color gradient manufactured according to the example was illustrated in FIG. 3.

As illustrated in FIG. 3, the zirconia block manufactured according to the example has the color gradient and has a shape in which colors sequentially change from the bottom to the top.

Preferred examples of the present invention have been described above in detail, but the present invention is not limited to the examples. The present invention may be modified by those skilled in the art in various forms without departing from the scope of the present invention.

According to a method of manufacturing a zirconia block having a color gradient of the present invention, a color gradient of a natural tooth is implemented in the zirconia block itself. Therefore, it is possible to express aesthetics of the natural tooth without using porcelain powder or a liquid color set, which has industrial applicability.

REFERENCE NUMERALS

10: mold
20: upper punch
30: lower punch
40: mold frame

The invention claimed is:

1. A method of manufacturing a zirconia block for an artificial tooth having a color gradient, comprising:
   (a) preparing colored zirconia-based powder and white zirconia-based powder;
   (b) preparing a plurality of raw materials in which the colored zirconia-based powder and the white zirconia-based powder are mixed in different weight ratios by mixing the colored zirconia-based powder and the white zirconia-based powder while changing a mixing ratio in order to express a desired color gradient;
   (c) sequentially injecting the plurality of raw materials into a compression mold in increasing or decreasing order of content of the colored zirconia-based powder of the raw material;
   (d) applying a pressure to the compression mold into which the plurality of raw materials are injected to mold;
   (e) performing a de-binding process in order to remove an organic binder from a molding result; and
   (f) calcining the molding result after the de-binding process,
   wherein the de-binding process is performed at a temperature of 400 to 800° C.

2. The method of claim 1, further comprising performing a cold isostatic pressing (CIP) process in order to maintain a uniform internal density distribution of the molding result before the calcining, wherein a cold isostatic pressure in a range of 10 to 200 MPa is applied to the molding result.

3. The method of claim 1,
wherein the colored zirconia-based powder is mixed with an organic binder and the organic binder being 0.1 to 7 parts by weight is mixed relative to 100 parts by weight of the colored zirconia-based powder, and
the white zirconia-based powder is mixed with the organic binder, and the organic binder being 0.1 to 7 parts by weight is mixed relative to 100 parts by weight of the white zirconia-based powder.

4. The method of claim 1,
wherein, when the colored zirconia-based powder and the white zirconia-based powder are mixed in order to prepare the plurality of raw materials, the organic binder is mixed together, and
the organic binder being 0.1 to 7 parts by weight is mixed relative to 100 parts by weight of each raw material.

5. The method of claim 1,
wherein, in order to express the color gradient, the plurality of raw materials include 7 to 20 raw materials in which the colored zirconia-based powder and the white zirconia-based powder are mixed in different ratios, and
the molding result has a structure in which the 7 to 20 raw materials are sequentially stacked.

6. The method of claim 1,
wherein, when the plurality of raw materials are observed as a whole,
content of the colored zirconia-based powder increases in a constant rate and content of the white zirconia-based powder corresponding to the content of the colored zirconia-based powder decreases in a constant rate, or content of the colored zirconia-based powder decreases in a constant rate and content of the white zirconia-based powder corresponding to the content of the colored zirconia-based powder increases in a constant rate, and
in the operation (c), the plurality of raw materials are sequentially injected in order of increasing content of the colored zirconia-based powder in a constant rate and decreasing content of the white zirconia-based powder corresponding to the content of the colored zirconia-based powder in a constant rate, or are sequentially injected in order of decreasing content of the colored zirconia-based powder in a constant rate and increasing content of the white zirconia-based powder corresponding to the content of the colored zirconia-based powder in a constant rate.

7. The method of claim 1,
wherein the colored zirconia-based powder is powder formed such that zirconia powder and a metal oxide for expressing colors are mixed and go through a sintering process, and
the metal oxide is made of at least one material selected from among red iron oxide ($Fe_2O_3$), yellow iron oxide ($Fe_2O_3$), $MoO_3$, $MnO_2$, $CeO_2$, $BaO$, $V_2O_5$, $V_2O_3$, and $CoO$.

8. The method of claim 1,
wherein the calcining is performed at a temperature of 800 to 1100° C. under an oxidizing atmosphere.

9. A method of manufacturing a zirconia block for an artificial tooth having a color gradient, comprising:
   (a) preparing colored zirconia-based powder and white zirconia-based powder;

(b) preparing a plurality of raw materials in which the colored zirconia-based powder and the white zirconia-based powder are mixed in different weight ratios by mixing the colored zirconia-based powder and the white zirconia-based powder while changing a mixing ratio in order to express a desired color gradient;

(c) sequentially injecting the plurality of raw materials into a mold frame along with a liner to mold in increasing or decreasing order of content of the colored zirconia-based powder of the raw material;

(d) de-molding a molding result from the mold frame;

(e) performing a de-binding process in order to remove the organic binder from the molding result; and (e) calcining the de-molded mold result after the de-binding process, wherein the de-binding process is performed at a temperature of 400 to 800° C.

10. The method of claim 9, further comprising performing a cold isostatic pressing (CIP) process in order to maintain a uniform internal density distribution of the molding result before the calcining, wherein a cold isostatic pressure in a range of 10 to 200 MPa is applied to the molding result.

11. The method of claim 9, wherein the colored zirconia-based powder is mixed with an organic binder and the organic binder being 0.1 to 7 parts by weight is mixed relative to 100 parts by weight of the colored zirconia-based powder, and the white zirconia-based powder is mixed with the organic binder and the organic binder being 0.1 to 7 parts by weight is mixed relative to 100 parts by weight of the white zirconia-based powder.

12. The method of claim 9, wherein, when the colored zirconia-based powder and the white zirconia-based powder are mixed in order to prepare the plurality of raw materials, the organic binder is mixed together, and the organic binder being 0.1 to 7 parts by weight is mixed relative to 100 parts by weight of each raw material.

13. The method of claim 9, wherein, in order to express the color gradient, the plurality of raw materials include 7 to 20 raw materials in which the colored zirconia-based powder and the white zirconia-based powder are mixed in different ratios, and the molding result has a structure in which the 7 to 20 raw materials are sequentially stacked.

14. The method of claim 9, wherein, when the plurality of raw materials are observed as a whole, content of the colored zirconia-based powder increases in a constant rate and content of the white zirconia-based powder corresponding to the content of the colored zirconia-based powder decreases in a constant rate, or content of the colored zirconia-based powder decreases in a constant rate and content of the white zirconia-based powder corresponding to the content of the colored zirconia-based powder increases in a constant rate, and in the operation (c), the plurality of raw materials are sequentially injected in order of increasing content of the colored zirconia-based powder in a constant rate and decreasing content of the white zirconia-based powder corresponding to the content of the colored zirconia-based powder in a constant rate, or are sequentially injected in order of decreasing content of the colored zirconia-based powder in a constant rate and increasing content of the white zirconia-based powder corresponding to the content of the colored zirconia-based powder in a constant rate.

15. The method of claim 9, wherein the colored zirconia-based powder is powder formed such that zirconia powder and a metal oxide for expressing colors are mixed and go through a sintering process, and the metal oxide is made of at least one material selected from among red iron oxide ($Fe_2O_3$), yellow iron oxide ($Fe_2O_3$), $MoO_3$, $MnO_2$, $CeO_2$, $BaO$, $V_2O_5$, $V_2O_3$, and $CoO$.

16. The method of claim 9, wherein the calcining is performed at a temperature of 800 to 1100° C. under an oxidizing atmosphere.

17. The method of claim 1, wherein the white zirconia-based powder has a spherical shape, and an average particle size of the white zirconia-based powder is about 0.2 μm.

18. The method of claim 9, wherein the white zirconia-based powder has a spherical shape, and an average particle size of the white zirconia-based powder is about 0.2 μm.

* * * * *